US010154964B2

(12) United States Patent
Villa et al.

(10) Patent No.: US 10,154,964 B2
(45) Date of Patent: *Dec. 18, 2018

(54) CONTROLLED RELEASE AND TASTE MASKING ORAL PHARMACEUTICAL COMPOSITION

(71) Applicant: COSMO TECHNOLOGIES LIMITED, Dublin (IE)

(72) Inventors: Roberto Villa, Lecco (IT); Massimo Pedrani, Gignese (IT); Mauro Ajani, Milan (IT); Lorenzo Fossati, Milan (IT)

(73) Assignee: COSMO TECHNOLOGIES LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/034,664

(22) Filed: Jul. 13, 2018

(65) Prior Publication Data

US 2018/0318225 A1 Nov. 8, 2018

Related U.S. Application Data

(63) Continuation of application No. 15/646,585, filed on Jul. 11, 2017, now Pat. No. 10,052,286, which is a continuation of application No. 15/368,911, filed on Dec. 5, 2016, now Pat. No. 9,737,489, which is a continuation of application No. 15/202,962, filed on Jul. 6, 2016, now Pat. No. 9,592,203, which is a continuation of application No. 14/832,845, filed on Aug. 21, 2015, now abandoned, which is a continuation of application No. 14/491,363, filed on Sep. 19, 2014, now Pat. No. 9,192,581, which is a continuation of application No. 13/585,190, filed on Aug. 14, 2012, now Pat. No. 9,132,093, which is a continuation-in-part of application No. 13/226,758, filed on Sep. 7, 2011, now Pat. No. 8,895,064.

(51) Int. Cl.
| | |
|---|---|
| *A61K 9/20* | (2006.01) |
| *A61K 9/28* | (2006.01) |
| *A61K 31/58* | (2006.01) |
| *A61K 9/00* | (2006.01) |
| *A61K 9/24* | (2006.01) |
| *A61K 9/16* | (2006.01) |

(52) U.S. Cl.
CPC .......... *A61K 9/2081* (2013.01); *A61K 9/0053* (2013.01); *A61K 9/209* (2013.01); *A61K 9/2013* (2013.01); *A61K 9/2018* (2013.01); *A61K 9/2027* (2013.01); *A61K 9/2054* (2013.01); *A61K 9/2077* (2013.01); *A61K 9/28* (2013.01); *A61K 9/282* (2013.01); *A61K 9/2806* (2013.01); *A61K 9/2813* (2013.01); *A61K 9/2846* (2013.01); *A61K 9/2866* (2013.01); *A61K 31/58* (2013.01); *A61K 9/1617* (2013.01); *A61K 9/1652* (2013.01); *A61K 9/2045* (2013.01)

(58) Field of Classification Search
None
See application file for complete search history.

(56) References Cited

U.S. PATENT DOCUMENTS

| | | |
|---|---|---|
| 3,133,863 A | 5/1964 | Tansey et al. |
| 3,800,051 A | 3/1974 | Barnhart et al. |
| 3,965,256 A | 6/1976 | Leslie |
| 4,608,248 A | 8/1986 | Knecht et al. |
| 4,716,041 A | 12/1987 | Kjornaes et al. |
| 5,183,815 A | 2/1993 | Saari et al. |
| 5,320,848 A | 6/1994 | Geyer et al. |
| 5,342,625 A | 8/1994 | Hauer et al. |
| 5,447,729 A | 9/1995 | Belenduik et al. |
| 5,472,711 A | 12/1995 | Baichwal |
| 5,534,501 A | 7/1996 | Samain et al. |
| 5,541,170 A | 7/1996 | Rhodes et al. |
| 5,597,844 A | 1/1997 | Chauhan et al. |
| 5,643,602 A | 7/1997 | Ulmius |
| 5,681,584 A | 10/1997 | Savastano et al. |
| 5,741,524 A | 4/1998 | Staniforth et al. |
| 5,811,388 A | 9/1998 | Friend et al. |
| 5,840,332 A | 11/1998 | Lerner et al. |
| 5,849,327 A | 12/1998 | Berliner et al. |
| 5,858,998 A | 1/1999 | Leuschner |

(Continued)

FOREIGN PATENT DOCUMENTS

| | | |
|---|---|---|
| CA | 2119253 | 11/1998 |
| CA | 2274943 A1 | 12/1999 |

(Continued)

OTHER PUBLICATIONS

Kshirsagar, S.J. et al., "In Vitro In Vivo Comparison of Two pH Sensitive Eudragit Polymers for Colon Specific Drug Delivery," Journal of Pharmaceutical Sciences and Research, 2009, vol. 1, No. 4, pp. 61-70.

(Continued)

*Primary Examiner* — Susan T Tran

(74) *Attorney, Agent, or Firm* — Rothwell, Figg, Ernst & Manbeck, P.C.

(57) ABSTRACT

Controlled release and taste masking compositions containing one or more active principles inglobated in a three-component matrix structure, i.e. a structure formed by successive amphiphilic, lipophilic or inert matrices and finally inglobated or dispersed in hydrophilic matrices. The use of a plurality of systems for the control of the dissolution of the active ingredient modulates the dissolution rate of the active ingredient in aqueous and/or biological fluids, thereby controlling the release kinetics in the gastrointestinal tract.

30 Claims, No Drawings

(56) References Cited

U.S. PATENT DOCUMENTS

| | | | |
|---|---|---|---|
| 5,863,910 A | 1/1999 | Bolonick et al. |
| 5,874,063 A | 2/1999 | Briggner et al. |
| 5,891,474 A | 4/1999 | Busetti et al. |
| 5,908,833 A | 6/1999 | Brattsand et al. |
| 5,955,502 A | 9/1999 | Hansen et al. |
| 5,965,167 A | 10/1999 | Sanghvi et al. |
| 6,004,582 A | 12/1999 | Faour et al. |
| 6,042,847 A | 3/2000 | Kerč et al. |
| 6,140,308 A | 10/2000 | Brattsand et al. |
| 6,190,692 B1 | 2/2001 | Busetti et al. |
| 6,214,378 B1 | 4/2001 | Tanida et al. |
| 6,239,120 B1 | 5/2001 | Hallgren et al. |
| 6,258,377 B1 | 7/2001 | New et al. |
| 6,368,629 B1 | 4/2002 | Watanabe et al. |
| 6,368,635 B1 | 4/2002 | Akiyama et al. |
| 6,562,363 B1 | 5/2003 | Mantelle et al. |
| 6,607,751 B1 | 8/2003 | Odidi et al. |
| 7,410,651 B2 | 8/2008 | Villa et al. |
| 7,410,652 B2 | 8/2008 | Villa et al. |
| 7,431,943 B1 | 10/2008 | Villa et al. |
| 8,029,823 B2 | 10/2011 | Villa et al. |
| 8,293,273 B2 | 10/2012 | Villa et al. |
| 8,545,811 B2 | 10/2013 | Moro et al. |
| 8,642,082 B2 | 2/2014 | Ajani et al. |
| 8,784,888 B2 | 7/2014 | Villa et al. |
| 8,895,064 B2 | 11/2014 | Villa et al. |
| 9,132,093 B2 | 9/2015 | Villa et al. |
| 9,192,581 B2 | 11/2015 | Villa et al. |
| 9,320,716 B2 | 4/2016 | Villa et al. |
| 2005/0020539 A1 | 1/2005 | Ajani et al. |
| 2005/0089571 A1 | 4/2005 | Beckert et al. |
| 2006/0003006 A1 | 1/2006 | Remon et al. |
| 2006/0057200 A1 | 3/2006 | Schaeffler |
| 2006/0134208 A1 | 5/2006 | Villa et al. |
| 2009/0011010 A1 | 1/2009 | Villa et al. |
| 2010/0305076 A1 | 12/2010 | Yen et al. |
| 2011/0123460 A1 | 5/2011 | Wilhelm et al. |
| 2012/0021052 A1 | 1/2012 | Villa et al. |
| 2012/0021053 A1 | 1/2012 | Villa et al. |
| 2012/0213850 A1 | 8/2012 | Villa et al. |
| 2012/0220559 A1 | 8/2012 | Villa et al. |
| 2012/0309959 A1 | 12/2012 | Villa et al. |
| 2012/0321710 A1 | 12/2012 | Villa et al. |
| 2013/0022679 A1 | 1/2013 | Villa et al. |
| 2013/0053360 A1 | 2/2013 | Villa et al. |
| 2014/0302139 A1 | 10/2014 | Villa et al. |
| 2014/0302143 A1 | 10/2014 | Villa et al. |
| 2015/0010629 A1 | 1/2015 | Villa et al. |
| 2015/0056279 A1 | 2/2015 | Villa et al. |

FOREIGN PATENT DOCUMENTS

| | | | |
|---|---|---|---|
| DE | 4131562 A1 | 3/1993 |
| EP | 0375063 B1 | 8/1990 |
| EP | 0453001 A1 | 10/1991 |
| EP | 0482576 A1 | 10/1991 |
| EP | 0514008 A1 | 4/1992 |
| EP | 1607087 A1 | 12/2005 |
| GB | 935639 | 9/1963 |
| JP | 63-048226 A1 | 2/1988 |
| JP | 4159217 A1 | 6/1992 |
| JP | 5132416 A1 | 5/1993 |
| JP | H06511478 A | 12/1994 |
| JP | H08503482 A | 4/1996 |
| JP | 2683575 B2 | 12/1997 |
| JP | 2948317 B2 | 9/1999 |
| JP | 2000510488 T | 8/2000 |
| JP | 20000515130 T | 11/2000 |
| WO | 9216206 A1 | 10/1992 |
| WO | 9221328 A1 | 12/1992 |
| WO | 9300889 A1 | 1/1993 |
| WO | 9305768 A1 | 4/1993 |
| WO | 9412180 A1 | 6/1994 |
| WO | 9516451 A1 | 6/1995 |
| WO | 9613273 A1 | 5/1996 |
| WO | 9636318 A2 | 11/1996 |
| WO | 9800169 A1 | 1/1998 |
| WO | 9911245 A1 | 3/1999 |
| WO | 9917752 A1 | 4/1999 |
| WO | 9939700 A1 | 8/1999 |
| WO | 0024388 A2 | 5/2000 |
| WO | 0076481 A1 | 6/2000 |
| WO | 0076478 A1 | 12/2000 |
| WO | 2010144865 A2 | 12/2010 |
| WO | 2011024122 A1 | 3/2011 |
| WO | 2012052918 A1 | 4/2012 |

OTHER PUBLICATIONS

Lichtenstein, G. et al., Poster, "Effect of Budesonide MMX 6 mg on the Hypothalamic-Pituitary-Adrenal (HPA) Axis in Patients with Ulcerative Colitis: Results from Phase III, 12 Month Safety and Extended User Study," May 2012, San Diego, CA, 1 page.

Sandborn, W.J. et al, "Once-Daily Budesonide MMX Extended Release Tablets Induce Remission in Patients With Mild to Moderate Ulcerative Colitis: Results From the CORE I Study," Gastroenterology 2012, vol. 143, pp. 1218-1226.

Travis, S. et al., Poster, "Induction of Clinical and Endoscopic Remission with Budesonide MMX in Mild-to-Moderately Active Ulcerative Colitis, Magnitude of Response in Two Phase III Studies," Oct. 20-24, 2012, Amsterdam, UEG Week, 1 page.

Campieri, M. et al., "Oral Budesonide is as Effective as Oral Prednisolone in Active Crohn's Disease," Gut, 1997, vol. 41, pp. 209-214.

O'Haens et al., poster: "Budesonide MMX is Efficient and Safe in Patients with Active Left-Sided Ulcerative Colitis," ECCO Congress (European Crohn's and Colitis Organisation), Innsbruck, Austria, Mar. 1-3, 2007, 1 page.

O'Haens et al., poster: "Safety and Efficacy of a Novel Extended Release Budesonide Formulation in Patients with Active Left-Sided Ulcerative Colitis," Digestive Disease Week, Washington, D.C., USA, May 19-24, 2007, 1 page.

Genticc Engineering & Biotechnology News | News Highlight Positive Phase III Data Leads Cosmo to Project U.S. and EU Filing for UC Drug in 2011; Nov. 8, 2010, 1 page.

Nicholls, A., "Bioavailability Profile of Uceris MMX Extended-Release Tablets Compared with Entocort EC Capsules in Healthy Volunteers," Journal of International Medical Research, 0(0), pp. 1-9, copyright The Author(s) 2013.

Handbook of Pharmaceutical Excipients, Sixth Edition, Rowe, R.C. et al., Eds., Pharmaceutical Press and American Pharmacists Association, London, 2009,14 pages, including pp. 385-387 and 697-699.

Santarus Submits IND for Phase III Clinical Testing of Rifamycin SV MMX in Travelers' Diarrhea, Dec. 30, 2009.

Spurio et al., "Low Bioavailability and Traditional Systemic Steroids in IBD: Can the Former Take Over the Latter?," Journal of Gastrointestinal and Liver Diseases, Mar. 2013, vol. 22, No. 1, pp. 65-71.

Travis et al., "Once-Daily Budesonide MMX in Active, Mild-to-Moderate Ulcerative Colitis: Results From the Randomised Core II Study," Gut, published online Feb. 22, 2013, doi: 10.1136/gutjnl-2012-304258, 9 pages.

Remington, The Science and Practice of Pharmacy, 21st Edition, Part 6—Pharmacodynamics and Pharmacokinetics, Chapter 58: Basic Pharmacokinetics and Pharmacodynamics, pp. 1180-1183, Lippincott Williams & Wilkins, Philadelphia, 2006, 8 pages total, including pp. 1180-1183.

JP Office Action dated May 6, 2010 from corresponding JP2001-502812—English translation included.

Sandborn, et al., "Induction of Clinical and Endoscopic Remission of Mild to Moderately Active Ulcerative Colitis with Budesonide MMX 9mg: Analysis of Pooled Data from Two Phase 3 Studies," poster, 1 page, presented Oct. 2011 at ECCO (European Crohn's and Colitis Organisation).

McNally, P.R., "Literature Review: Core I & II: COlonic RElease Budesonide for the Induction of Remission for Mild-Moderate Ulcerative Colitis," Visible Human Journal of Endoscopy, vol. 13, Issue 1, 2014, 5 pages.

(56) References Cited

OTHER PUBLICATIONS

Steward, P., "Review of Pharmaceutical Controlled Release Methods and Devices," 1995, pp. 1-9.
Physical Pharmacy, Chapter 19: Drug Product Design, 1993, pp. 515-519.
Moro, et al., "Drug Delivery Systems: Diffusion Controlled Systems," Il Prodotto Chimico & Aerosol Selezione (The Chemical & Aerosol Selection), Apr. 1985, pp. 16-24.
Porro, G.B. et al., "Comparative Trial of Methylprednisolone and Budesonide Enemas in Active Distal Ulcerative Colitis," European Journal of Gastroenterology & Hepatology, 1994, vol. 6, No. 2, pp. 125-130, © Current Science Ltd.
McLeod, A.D. et al., "Kinetic Perspectives in Colonic Drug Delivery," in Oral Colon-Specific Drug Delivery, pp. 106-108, (David R. Friend ed., CRC Press 1992).
O'Haens, B.R. et al., "Clinical Trial: Preliminary Efficacy and Safety Study of a New Budesonide-MMX® 9mg Extended-Release Tablets in Patients with Active Left-Sided Ulcerative Colitis," Journal of Crohn's and Colitis, 2010, vol. 4, pp. 153-160, © 2009 European Crohn's and Colitis Organisation.
Jantzen, G.M. et al., "Sustained- and Controlled Release Drug Delivery Systems," Modern Pharmaceutics, 3rd Edition, Revised and Expanded, pp. 575-609, © 1996 by Marcel Dekker, Inc., 37 pages.
Angelucci et al., "Budesonide for Inflammatory Bowel Disease Treatment," Current Medicinal Chemistry, 2008, vol. 15, No. 14, pp. 2-9.
O'Haens, G.R. et al., Abstract: "Budesonide MMX™ Is Active and Safe in Patients With Active Left-Sided Ulcerative Colitis," J Crohn's and Colitis Supplements vol. 1, p. 14, P043, Mar. 2007, 1 page.
Maejima, T., "Application of Tumbling Melt Granulation Method to Prepare Controlled Release Beads by Coating with Mixture of Functional Non-Meltable and Meltable Materials," Chem. Pharm. Bull., 1998, vol. 48, No. 3, pp. 531-533, © 1998 Pharmaceutical Society of Japan.
Sandborn, W.J., Abstract: "Budesonide MMX® 9 mg for the Induction of Remission of Mild-to-Moderate Ulcerative colitis (UC): Data From a Multicenter, Randomized Double-Blind Placebo-Controlled Study in North America and India," Digestive Diseases Week, Abstract 746, Gastroenterology 140(5) S-124, 2011.
Sandborn, W.J. et al., Poster: "Budesonide MMX® 9 mg for the Induction of Remission of Mild-to-Moderate Ulcerative Colitis (UC): Data From a Multicenter, Randomized Double-Blind Placebo-Controlled Study in North America and India," Digestive Disease Week, 2011, 1 page.
Flanders, P. et al., "TheControl of Drug Release From Conventional Melt-Granulation Matrices," Drug Development and Industrial Pharmacy, 1997, vol. 13, No. 6, pp. 1001-1022, © 1987 Marcel Dekker, Inc.
Ferraboschi, P. et al., "Estimation and Characterisation of Budesonide Tablets Impurities," Journal of Parmaceutical and Biomedical Analysis, 2008, vol. 47, pp. 636-649, © 2008 Elsevier B.V.
Fiorino, G. et al., "New Drug Delivery System in Inflammatory Bowel Disease: MMX™ and Tailored Delivery to the Gut," Current Medicinal Chemistry, 2010, vol. 17, pp. 1851-1857, © 2010 Bentham Science Publishers Ltd.
Koutroubakis, I., "Recent Advances in the Management of Distal Ulcerative Colitis," World Journal of Gastrointestinal Pharmacology and Therapeutics, 2010, vol. 1, No. 2, pp. 43-50, © 2010 Baishideng.

Brunner, M. et al., "Gastrointestinal Transit, Release and Plasma Pharmacokinetics of a New Oral Budesonide Formulation," British Journal of Clinical Pharmacology, vol. 61, pp. 31-38, © 2005 Blackwell Publishing Ltd.
Brunner, M. et al., "Gastrointestinal Transit and 5-ASA Release from a New Mesalazine Extended-Release Formulation," Alimentary Pharmacology and Therapeutics, vol. 17, pp. 395-402, © Blackwell Publishing Ltd., 8 pages.
Remington's Pharmaceutical Sciences (18th Edition 1990), p. 390, plus cover page.
Sandborn, W.J. et al., Abstract: "Budesonide MMX® 9 mg for the Induction of Remission of Mild-to-Moderate Ulcerative Colitis (UC): Data From a Multicenter, Randomized Double-Blind Placebo-Controlled Study in the Europe, Russia, Israel and Australia," Digestive Diseases Week, Abstract 292, Gastroenterology 140(5) S-65, 2011.
Sandborn, W.J. et al., "MMX Multi Matrix System mesalazine for the induction of remission in patients with mild-to-moderate ulcerative colitis: a combined analysis of two randomized, double-blind, placebo-controlled trials," Alimentary Pharmacol & Therapeut, vol. 26, pp. 205-215, 2007.
Akhgari, A. et al., "Statistical Optimization of Indomethacin Pellets Coated with pH-Dependent Methacrylic Polymers for Possible Colonic Drug Delivery," International Journal of Pharmaceutics, 305, (2005), pp. 22-30, copyright 2005 Elsevier B.V.
Baron et al. (International Union for Pure and Applied Chemistry, Glossary of class names of polymers based on chemical structure and molecular architecture, IUPAC Recommendations 2009, pp. 1-59).
Santarus, Inc., Investor Day Slides, May 13, 2009. 114 pages.
Keller et al., Oral budesonide therapy for steroid-dependent ulverative colitis: pilot trial, 1997, Aliment Pharmacal Ther, vol. 11, pp. 1047-1052.
Friend, "Review article: issues in oral administration of locally acting glucocorticosteroids for treatment of inflammatory bowel disease", Aliment Pharmacol Ther 12:591-603, 1998.
Greenberg et al., "Oral budesonide for active Crohn's disease", New Eng J Med 331:836-841, 1994.
Lofberg et al., "Oral budesonide versus prednisolone in patients with active extensive and left-sided ulcerative colitis", Gastroenterology 110:1713-1718, 1996.
Cheng et al., "Time- and pH-dependent colon-specific drug delivery for orally administered diclofenac sodium and 5-aminosalicylic acid", World J Gastroenterol 10:1769-1774, 2004.
Khan et al., "A pH-dependent colon-targeted oral drug delivery system using methacrylic acid copolymers. II. Manipulation of drug release using Eudragit L100 and Eudragit S100 combinations". Drug Dev Ind Pharm 26:549-554, 2000.
Hardy, J. G. et al. "Drug delivery to the proximal colon", Journal of Pharmacy and Pharmacology, 1985, pp. 874-877, vol. 37.
Rhodes, J. et al. "Inflammatory Bowel Disease Management: Some Thoughts on Future Drug Developments", Drugs, Feb. 1997, pp. 189-194, vol. 53, No. 2.
Russian Decision on Grant issued in Application No. 2014137128/15 dated Feb. 8, 2018, 8 pages.
L. Borgström et al. "Lung deposition of budesonide inhaled via Turbuhaler®: A comparison with terbutaline sulphate in normal subjects," Eur. Respir. J., 7:69-73 (1994)—pages.
Gliko-Kabir et al. "Low Swelling, Crosslinked Guar and Its Potential Use as a Colon-Specific Drug Carrier," Pharm. Research 15(7): 1019-1025 (1998)—pages.
M. Matsuo et al. "Evaluation of Hydroxyethylcellulose as a Hydrophilic Swellable Material for Delayed-Release Tablets," Chem. Pharm. Bull. 43(20):311-314 (1995)—pages.
Santarus, Inc., "Extension Study of Budesonide MMX™ 6mg in Maintenance of Remission in Patients With Ulcerative Colitis" ClinicalTrials.gov, updated Feb. 23, 2011(3 pages).

CONTROLLED RELEASE AND TASTE MASKING ORAL PHARMACEUTICAL COMPOSITION

CROSS-REFERENCE TO RELATED APPLICATIONS

This application is a continuation of U.S. patent application Ser. No. 15/646,585, filed Jul. 11, 2017, which in turn is a continuation of U.S. patent application Ser. No. 15/368,911, filed Dec. 5, 2016, now U.S. Pat. No. 9,737,489, which in turn is a continuation of U.S. patent application Ser. No. 15/202,962, filed Jul. 6, 2016, now U.S. Pat. No. 9,592,203, which in turn is a continuation of U.S. patent application Ser. No. 14/832,845, filed Aug. 21, 2015, now abandoned, which in turn is a continuation of U.S. patent application Ser. No. 14/491,363, filed Sep. 19, 2014, now U.S. Pat. No. 9,192,581, which in turn is a continuation of U.S. patent application Ser. No. 13/585,190, filed Aug. 14, 2012, now U.S. Pat. No. 9,132,093, which in turn is a continuation-in-part of U.S. patent application Ser. No. 13/226,758, filed Sep. 7, 2011, now U.S. Pat. No. 8,895,064. Each application is incorporated herein by reference in its entirety.

The present invention relates to controlled release, delayed release, prolonged release, extended release and/or taste masking compositions containing budesonide as active ingredient incorporated in a three-component matrix structure, i.e. a structure formed by successive amphiphilic, lipophilic or inert matrices and finally incorporated or dispersed in hydrophilic matrices. The use of a plurality of systems mechanism for the control of the dissolution of the active ingredient modulates the dissolution rate of the active ingredient in aqueous and/or biological fluids, thereby controlling the release kinetics in the gastrointestinal tract, and it also allows the oral administration of active principles having unfavorable taste characteristics or irritating action on the mucosae of the administration site, particularly in the buccal or gastric area.

The compositions of the invention are suitable to the oral administration or the efficaciously deliver the active ingredient acting topically at some areas of the gastrointestinal tract.

TECHNOLOGICAL BACKGROUND

The preparation of a sustained, controlled, delayed, extended or anyhow modified release form can be carried out according to different techniques:
1. The use of inert matrices, in which the main component of the matrix structure opposes some resistance to the penetration of the solvent due to the poor affinity towards aqueous fluids; such property being known as lipophilia.
2. The use of hydrophilic matrices, in which the main component of the matrix structure opposes high resistance to the progress of the solvent, in that the presence of strongly hydrophilic groups in its chains, mainly branched, remarkably increases viscosity inside the hydrated layer.
3. The use of bioerodible matrices, which are capable of being degraded by the enzymes of some biological compartment.

All the procedures listed above suffer, however, from drawbacks and imperfections.

Inert matrices, for example, generally entail non-linear, but exponential, release of the active ingredient.

Hydrophilic matrices: have a linear behaviour until a certain fraction of active ingredient has been released, then significantly deviate from linear release.

Bioerodible matrices are ideal to carry out the so-called "sire-release", but they involve the problem of finding the suitable enzyme or reactive to degradation. Furthermore, they frequently release in situ metabolites that are not wholly toxicologically inert.

A number of formulations based on inert lipophilic matrices have been described: Drug Dev. Ind. Pharm. 13 (6), 1001-1022, (1987) discloses a process making use of varying amounts of colloidal silica as a porization element for a lipophilic inert matrix in which the active ingredient is incorporated.

The same notion of canalization of an inert matrix is described in U.S. Pat. No. 4,608,248 in which a small amount of a hydrophilic polymer is mixed with the substances forming an inert matrix, in a non sequential compenetration of different matrix materials. EP 375,063 discloses a technique for the preparation of multiparticulate granules for the controlled-release of the active ingredient which comprises co-dissolution of polymers or suitable substances to form a inert matrix with the active ingredient and the subsequent deposition of said solution on an inert carrier which acts as the core of the device. Alternatively, the inert carrier is kneaded with the solution containing the inert polymer and the active ingredient, then the organic solvent used for the dissolution is evaporated off to obtain a solid residue. The resulting structure is a "reservoir", i.e. is not macroscopically homogeneous along all the symmetry axis of the final form. The same "reservoir" structure is also described in Chem. Pharm. Bull. 46 (3), 531-533, (1998) which improves the application through an annealing technique of the inert polymer layer which is deposited on the surface of the pellets.

To the "reservoir" structure also belong the products obtained according to the technique described in WO 93/00889 which discloses a process for the preparation of pellets in hydrophilic matrix which comprises: —dissolution of the active ingredient with gastro resistant hydrophilic polymers in organic solvents; —drying of said suspension; —subsequent kneading and formulation of the pellets in a hydrophilic or lipophilic matrix without distinction of effectiveness between the two types of application. EP 0 453 001 discloses a multiparticulate with "reservoir" structure inserted in a hydrophilic matrix. The basic multiparticulate utilizes two coating membranes to decrease the release rate of the active ingredient, a pH-dependent membrane with the purpose of gastric protection and a pH-independent methacrylic membrane with the purpose of slowing down the penetration of the aqueous fluid. WO 95/16451 discloses a composition only formed by a hydrophilic matrix coated with a gastro-resistant film for controlling the dissolution rate of the active ingredient. When preparing sustained-, controlled-release dosage forms of a medicament topically active in the gastrointestinal tract, it is important to ensure a controlled release from the first phases following administration, i.e. when the inert matrices have the maximum release rate inside the logarithmic phase, namely the higher deviation from linear release. Said object has been attained according to the present invention, through the combination of an amphiphilic matrix inside an inert matrix, the latter formulated with a lipophilic polymer in a superficial hydrophilic matrix. The compositions of the invention are characterized by the absence of a first phase in which the medicament superficially present on the matrix is quickly solubilized, and by the fact the amphiphilic layer compensate the lack of affinity of the aqueous solvent with the lipophilic compounds forming the inner inert matrix.

DISCLOSURE OF THE INVENTION

The invention provides controlled release, delayed release, prolonged release, extended release and/or taste masking oral pharmaceutical compositions containing as active ingredient budesonide comprising:
- a) a matrix consisting of lipophilic compounds with melting point lower than 90° C. and optionally by amphiphilic compounds in which the active ingredient is at least partially incorporated;
- b) an amphiphilic matrix;
- c) an outer hydrophilic matrix in which the lipophilic matrix and the amphiphilic matrix are dispersed;
- d) optionally other excipients.

A particular aspect of the invention consists of controlled release, delayed release, prolonged release, extended release and/or taste masking oral compositions containing as active ingredient budesonide comprising:
- a) a matrix consisting of amphiphilic compounds and lipophilic compounds with melting point below 90° C. in which the active ingredient is at least partially incorporated;
- b) an outer hydrophilic matrix in which the lipophilic/amphiphilic matrix is dispersed, preferably by mixing;
- c) optionally other excipients.

According to a preferred embodiment of the invention, the active ingredient budesonide is contained in the composition in an amount from 1.5% to 15% w/w, based on the total weight of the composition. According to a preferred embodiment of the invention, budesonide is comprised in an amount from 5 to 10 mgs/dose unit, more preferably in an amount of about 6 mgs/dose unit or 9 mgs/dose unit.

A further aspect of the invention provides taste masking oral pharmaceutical compositions budesonide containing comprising:
- an inert or lipophilic matrix consisting of C6-C20 alcohols or C8-C20 fatty acids or esters of fatty acids with glycerol or sorbitol or other polyalcohols with carbon atom chain not higher than six;
- an amphiphilic matrix consisting of polar lipids of type I or II or glycols partially etherified with C1-C4 alkyl chains;
- an outer hydrophilic matrix containing the above matrices, mainly formed by saccharide, dextrin, polyalcohol or cellulose compounds or by hydrogels or their mixtures;
- optional excipients to give stability to the pharmaceutical formulation.

DETAILED DISCLOSURE OF THE INVENTION

The compositions of the invention can be prepared by a method comprising the following steps:
- a) the active ingredient, represented by budesonide, is first inglobated by simple kneading or mixing in a matrix or coating consisting of compounds having amphiphilic properties, which will be further specified below. The active ingredient can be mixed with the amphiphilic compounds without the aid of solvents or with small amounts of water-alcoholic solvents.
- b) the matrix obtained as specified under a) is incorporated in a low melting lipophilic excipient or mixture of excipients, if necessary while heating to soften and/or melt the excipient itself, which thereby incorporates the active ingredient by simple dispersion, forming an inert matrix which can be reduced in size to obtain inert matrix granules containing the active ingredient particles.
- c) the inert matrix granules are subsequently mixed together with one or more hydrophilic water-swellable excipients. The mixture is then subjected to compression or tableting. This way, when the tablet is contacted with biological fluids, a high viscosity swollen layer is formed, which coordinates the solvent molecules and acts as a barrier to penetration of the aqueous fluid itself inside the new structure. Said barrier antagonizes the starting "burst effect" caused by the dissolution of the medicament inglobated inside the inert matrix, which is in its turn inside the hydrophilic matrix.

The amphiphilic compounds which can be used according to the invention comprise polar lipids of type I or II (lecithin, phosphatidylcholine, phosphatidylethanolamine), ceramides, glycol alkyl ethers such as diethylene glycol monomethyl ether (Transcutol®).

The lipophilic matrix consists of substances selected from unsaturated or hydrogenated alcohols or fatty acids, salts, esters or amides thereof, fatty acids mono-, di- or triglycerides, the polyethoxylated derivatives thereof, waxes, ceramides, cholesterol derivatives or mixtures thereof having melting point within the range of 40° to 90° C., preferably from 60° to 70° C. If desired, a fatty acid calcium salt may be incorporated in the lipophilic matrix which is subsequently dispersed in a hydrophilic matrix prepared with alginic acid, thus remarkably increasing the hydrophilic matrix viscosity following penetration of the solvent front until contact with the lipophilic matrix granules dispersed inside.

An amphiphilic matrix with high content in active ingredient, typically from 5% to 95% w/w, in particular from 20% to 70%, or from 1.5% to 15% w/w, is first prepared by dispersing the active ingredient in a mixture of amphiphilic compounds, such as lecithin, other type II polar lipids, surfactants, or in diethylene glycol monoethyl ether; the resulting amphiphilic matrix is then mixed or kneaded, usually while hot, with lipophilic compounds suitable to form an inert matrix, such as saturated or unsaturated fatty acids, such as palmitic, stearic, myristic, lauric, laurylic, or oleic acids or mixtures thereof with other fatty acids with shorter chain, or salts or alcohols or derivatives of the cited fatty acids, such as mono-, di-, or triglycerides or esters with polyethylene glycols, alone or in combination with waxes, ceramides, cholesterol derivatives or other apolar lipids in various ratios so that the melting or softening points of the lipophilic compounds mixtures is within the range of 40° to 90° C., preferably from 60° to 70° C. Alternatively, the order of formation of the inert and amphiphilic matrices can be reversed, incorporating the inert matrix inside the amphiphilic compounds. The resulting inert lipophilic matrix is reduced into granules by an extrusion and/or granulation process, or any other known processes which retain the homogeneous dispersion and matrix structure of the starting mixture.

The hydrophilic matrix consists of excipients known as hydrogels, i.e. substances which when passing from the dry state to the hydrated one, undergo the so-called "molecular relaxation", namely a remarkable increase in mass and weight following the coordination of a large number of water molecules by the polar groups present in the polymeric chains of the excipients themselves. Examples of hydrogels which can be used according to the invention are compounds selected from acrylic or methacrylic acid polymers or copolymers, alkylvinyl polymers, hydroxyalkyl celluloses, carboxyalkyl celluloses, polysaccharides, dextrins, pectins, starches and derivatives, natural or synthetic gums, alginic acid. In case of taste-masking formulations, the use of polyalcohols such as xylitol, maltitol and mannitol as hydrophilic compounds can also be advantageous.

The lipophilic matrix granules containing the active ingredient are mixed with the hydrophilic compounds cited above in a weight ratio typically ranging from 100:0.5 to 100:50 (lipophilic matrix:hydrophilic matrix). Part of the active ingredient can optionally be mixed with hydrophilic substances to provide compositions in which the active ingredient is dispersed both in the lipophilic and the hydrophilic matrix, said compositions being preferably in the form of tablets, capsules and/or minitablets. The compression of the mixture of lipophilic and/or amphiphilic matrix, hydrogel-forming compound and, optionally, active ingredient not inglobated in the lipophilic matrix, yields a macroscopically homogeneous structure in all its volume, namely a matrix containing a dispersion of the lipophilic granules in a hydrophilic matrix. A similar result can also be obtained by coating the lipophilic matrix granules with a hydrophilic polymer coating. The tablets obtainable according to the invention can optionally be subjected to known coating processes with a gastro-resistant film/gastro-resistant coating, consisting of, for example, acrylic and/or methacrylic acids polymers (Eudragit®) or copolymers (Eudragit S/L) or cellulose derivatives, such as cellulose acetophthalate/s.

According to a preferred embodiment of invention the gastro-protective coating can be represented by a mixture of acrylic and/or methacrylic acid copolymers type A and/or type B (as, for example, Eudragit S100 and/or Eudragit L100).

According to a further embodiment of the invention, the mixture of acrylic and/or methacrylic acid copolymers type A and/or type B is preferably in a range ratio from 1:5 to 5:1.

According to another further embodiment, the gastro-protective coating also optionally comprises plasticizers, dyes, at least one water-solvent, at least one organic solvent or a mixture thereof.

The composition of the invention can further contain conventional excipients, for example bioadhesive excipients such as chitosans, polyacrylamides, natural or synthetic gums, acrylic acid polymers. The compositions of the invention are preferably in the form of tablets, capsules or minitablets. In terms of dissolution characteristics, contact with water or aqueous fluids causes the immediate penetration of water inside the more superficial layer of the matrix which, thanks to the presence of the aqueous solvent, swells due to the distension of the polymeric chains of the hydrogels, giving rise to a high viscosity hydrated front which prevents the further penetration of the solvent itself linearly slowing down the dissolution process to a well determined point which can be located at about half the thickness, until the further penetration of water would cause the disintegration of the hydrophilic layer and therefore the release of the content which, consisting of inert matrix granules, however induces the diffusion mechanism typical of these structures and therefore further slows down the dissolution profile of the active ingredient. The presence of the amphiphilic matrix inside the lipophilic matrix inert allows to prevent any unevenness of the release profile of the active ingredient. The surfactants present in the amphiphilic portion promote wettability of the porous canaliculuses which cross the inert matrix preventing or reducing resistance to penetration of the solvent inside the inert matrix. To obtain taste masking tablets, the components of the hydrophilic matrix are carefully selected to minimize the active substance release time through penetration accelerated by the canalization induced by the hydrophilic compound.

The compositions of the present invention are preferably intended for use in the treatment of subjects suffering from Inflammatory Bowel Disease and/or Irritable Bowel Syndrome. Preferably, according to the invention Inflammatory Bowel Disease is Crohn's disease or Ulcerative Colitis.

Further object of the invention is then a method for the treatment of a subject suffering from Inflammatory Bowel Disease and/or Irritable Bowel Syndrome comprising administering a pharmaceutical composition comprising an effective amount of budesonide, as above defined and disclosed, to a subject in need of such treatment. Preferably, according to the invention Inflammatory Bowel Disease is Crohn's disease or Ulcerative Colitis.

According to a preferred embodiment of the invention the budesonide composition release is:
below 15% within the first hour at pH 7.2,
greater than 80% within eight hours at pH 7.2.

According to a further preferred embodiment of the invention the budesonide composition release is:
below 15% within the first hour at pH 7.2,
below 25% within two hours at pH 7.2;
between 25% and 55% within four hours at pH 7.2;
greater than 80% within eight hours at pH 7.2.

According to a further preferred embodiment of the invention the budesonide composition release is:
below 15% with the first hour at pH 7.2,
between 20% and 60% within four hours at pH 7.2;
greater than 80% at eight hour at pH 7.2.

EXPERIMENTAL PART

To test the effective ability of the formulations of the invention to modify the release rate and extent of the active ingredient from the dosage form suitable for the drug administration, before any pharmacokinetic study on patients or volunteers, the dissolution test is taken as monitoring and discriminating tool (according to USP type II apparatus complying with USP <711>).

Also the bioavailability profile of the formulations of the invention is carried out, in comparison with a marketed formulation Entocort® EC 3×3 mg capsules. As preferred embodiment, the bioavailability study showed a $T_{max}$ average value higher than 8 hours and a MRT average value higher than 14 hours.

According to the invention, $T_{max}$ corresponds to "time to peak concentration", i.e., time to reach the peak plasma concentration of a drug after oral administration ($C_{max}$) and MRT corresponds to "mean residence time", i.e., the average total time molecules of a given dose spend in the body. This can only be measured after instantaneous administration.

Other pharmacokinetics parameters useful according to the invention are represented by:

AUC, which corresponds to "area under the curve", i.e., the integral of the concentration-time curve (after a single dose or in steady state). In particular, $AUC_{0-t}$ is the area under the curve up to the last point and $AUC_{0-\infty}$ is the area under the curve up to infinite.

$C_{max}$, which corresponds to "peak concentration", i.e., the peak plasma concentration of a drug after oral administration.

$t_{1/2}$, which corresponds to "biological half-time", i.e., the time required for the concentration of the drug to reach half of its original value.

$Xu_{0-36h}$ (ng), which corresponds to "urinary excretion", i.e., the active ingredient metabolite urinary excretion during 36 hours time.

$T_{lag}$, which corresponds to lag time, i.e., the time from administration of a drug to first quantifiable concentration.

CI, which corresponds to "confidence intervals", i.e., a particular kind of interval estimate of a population parameter used to indicate the reliability of an estimate.

CV, which corresponds to "coefficient of variation" provides a relative measure of data dispersion with reference to the mean.

Dissolution Test Method

Tablets according to the present invention undergo to dissolution test to verify the formulation capacity in modulating and controlling the rate by which the active ingredient is leaked by the device or dosage form in the environmental medium, generally a buffered solution simulating gastric or intestinal juices.

The dissolution test is performed by introducing individual tablets in a glace vessel containing from 500 to 1000 ml of a buffered solution set to different pH conditions (pH 1, 6.4 and 7.2 are the pH condition generally used in this test applications), so that the whole digestive tract pH conditions, from stomach to large intestine, should be reproduced. To simulate the human body conditions, the test is carried out at a temperature of 37° C.±2° C. and at predetermined time periods samples of the dissolution medium are withdrawn to detect the percentage of active ingredient dissolved over time.

The tablets according to the present invention, when designed to be used to treat inflammatory bowel disease, in principle have to show a good resistance, thanks to the polymeric film resistant to the low pH conditions (intended as <5 to simulate the gastric environment) applied to cover the tablet surface, resistance which last at least for two hours; to target the large intestinal sectors, also the pH condition of 6.4 shown unsuitability to determine a drug leakage from the administration device for a short exposition time and only mediums at pH 7.2 have been able to determine an active ingredient dissolution at a progressive and quite constant rate during a timeframe from 6 to 12 hours; the dissolution percentage obtained with this tablet formulation were below 15% at first hour sampling, below 25% at second hour sampling, then values were in the range 25% to 55% at fourth hour and a dissolution greater than 80% was achieved at $8^{th}$ hour sampling.

Bioavailability Study

Bioavailability profile of budesonide extended release compositions (6 mg and 9 mg tablets) vs. controlled ileal release formulation (Entocort® 3×3 mg capsules) in healthy volunteers is carried out. The objectives of the study are to compare the bioavailability and PK profile of a 9 mg budesonide extended release tablet formulation of the invention (herein after referred to as T1) versus the market reference formulation, Entocort® EC 3×3 mg capsules (Astra-Zeneca) (herein after referred to as R) and versus a 6 mg budesonide formulation of the invention (herein after referred to as T2).

The primary end-point is comparing bioavailability rate through the PK parameters of plasma budesonide $C_{max}$ and $T_{max}$ after T1 formulation versus reference formulation.

The secondary end-point is comparing bioavailability extent through plasma budesonide $AUC_{0-t}$ after T1 formulation versus reference formulation; comparing bioavailability extent through the PK parameters of plasma budesonide $AUC_{0-t}$ after T1 formulation versus T2 formulation; descriptive pharmacokinetics of budesonide; evaluation of main budesonide metabolite excretion in urine and safety of the test and reference formulations.

Budesonide MMX™ extended release tablets 9 mgs (T1) and 6 mgs (T2) were orally administered in a single dose under fasting conditions in different study periods with a wash-out interval of at least 5 days. One tablet of T1 (batch MV084) or T2 (batch TV158) was administered together with 240 mL of mineral water; the subjects were instructed to swallow the whole tablet without chewing.

The reference therapy was Entocort® EC 3×3 mg capsules (MP0077; Astra-Zeneca, Sweden), orally administered in a single dose under fasting conditions together with 240 mL of mineral water; the subjects were instructed to swallow the whole tablet without chewing.

Results:

After administration under fasting conditions in 3 consecutive study periods of a single dose of budesonide MMX™ extended release tablets 9 mg (T1), 6 mg (T2) of the invention and Entocort EC 3×3 mg capsules (R) the PK of budesonide was found significantly different. Mean±SD (CV %) of plasma budesonide and urine budesonide metabolite PK parameters are summarized in the Tables 1-4 below for the PP population (N=12) and PP-control population (N=11).

TABLE 1

Mean ± SD (CV %) Budesonide PK Parameters after Administration of T1, T2 and R

|  | MMX ™ 9 mg (T1) | MMX ™ 6 mg (T2) | Entocort ® EC 3 × 3 mg (R) |
|---|---|---|---|
| | PP-population (N = 12) | | |
| $T_{max}$ (h) | 13.3 ± 5.9 (44.5) | 11.4 ± 5.1 (44.4) | 4.8 ± 1.4 (28.6) |
| $C_{max}$ (pg/mL) | 1348.8 ± 958.8 (71.1) | 1158.5 ± 532.4 (46.0) | 1555.9 ± 588.0 (37.8) |
| $AUC_{0-t}$ (pg × h/mL) | 13555.9 ± 7816.9 (57.7) | 10818.3 ± 4401.6 (40.7) | 13394.6 ± 5983.0 (44.7) |
| $AUC_{0-\infty}$ (pg ×. h/mL) | 16431.2 ± 10519.8 (64.0) | 11533.6 ± 4738.5 (41.1) | 14057.0 ± 6378.7 (45.4) |
| $C_{max}$ (pg/mL)/dose | 149.9 ± 106.5 (71.1) | 193.1 ± 88.7 (46.0) | 172.9 ± 65.3 (37.8) |
| $AUC_{0-t}$ (pg × h/mL)/dose | 1506.2 ± 868.5 (57.7) | 1803.0 ± 733.6 (40.7) | 1488.3 ± 664.8 (44.7) |
| $t_{1/2}$ (h) | 8.2 ± 3.7 (44.7) | 6.6 ± 2.4 (36.8) | 7.7 ± 1.8 (23.1) |
| MRT (h) | 21.4 ± 6.8 (31.5) | 17.0 ± 5.7 (33.7) | 11.6 ± 2.7 (23.1) |
| | PP-control population (N = 11) | | |
| $T_{max}$ (h) | 12.8 ± 6.0 (46.7) | 11.0 ± 5.1 (46.4) | 4.6 ± 1.4 (29.4) |
| $C_{max}$ (pg/mL) | 1427.3 ± 964.3 (67.6) | 1154.9 ± 558.2 (48.3) | 1549.0 ± 616.2 (39.8) |
| $AUC_{0-t}$ (pg × h/mL) | 13963.7 ± 8063.4 (57.7) | 10331.4 ± 4264.1 (41.3) | 13741.1 ± 4147.5 (44.7) |
| $AUC_{0-\infty}$ (pg ×. h/mL) | 17041.8 ± 10807.8 (63.4) | 11533.6 ± 4738.5 (41.1) | 14462.8 ± 6572.3 (45.4) |
| $C_{max}$ (pg × h/mL)/dose | 158.6 ± 107.1 (67.6) | 192.5 ± 93.0 (48.3) | 172.1 ± 68.5 (39.8) |
| $AUC_{0-\infty}$ (pg × h/mL)/dose | 1551.5 ± 895.9 (57.7) | 1721.9 ± 710.7 (41.3) | 1526.8 ± 683.1 (44.7) |
| $t_{1/2}$ (h) | 8.4 ± 3.7 (44.0) | 6.6 ± 2.4 (36.8) | 7.9 ± 1.7 (21.0) |
| MRT (h) | 21.4 ± 7.1 (33.1) | 17.0 ± 5.7 (33.7) | 11.8 ± 2.7 (23.1) |

TABLE 2

Mean ± SD (CV %) 6-β-Hydroxy-budesonide Cumulative Excretion ($Xu_{0-36\,h}$) after Administration of T1, T2 and R

| | MMX™ 9 mg (T1) | MMX™ 6 mg (T2) | Entocort® EC3 × 3 mg (R) |
|---|---|---|---|
| | PP-population (N = 12) | | |
| $Xu_{0-36\,h}$ (ng) | 111061.9 ± 53992.6 (48.6) | 76683.4 ± 31879.4 (41.6) | 161535.4 ± 60309.8 (37.3) |
| $Xu_{0-36\,h}$ (ng)/dose | 12340.2 ± 5999.2 (48.6) | 12780.6 ± 5313.2 (41.6) | 17948.4 ± 6701.1 (37.3) |
| | PP-control population (N = 11) | | |
| $Xu_{0-36\,h}$ (ng) | 114449.9 ± 55273.9 (48.3) (43.7) (37.8) | 74729.9 ± 32673.4 | 164572.0 ± 62283.9 |
| $Xu_{0-36\,h}$ (ng)/dose | 12716.6 ± 6141.5 (48.3) (43.7) (37.8) | 12455.0 ± 5445.6 | 18285.8 ± 6920.4 |

TABLE 3

Main Individual and Mean Budesonide PK Parameters after Administration of MMX™ 9 mg Extended Release Tablets T1

| Subject | $T_{max}$ (h) | $C_{max}$ (pg/mL) | $AUC_{0-t}$ (pg × h/mL) | $AUC_{0-\infty}$ (pg × h/mL) | $t_{1/2}$ (h) | MRT (h) | $C_{max}$/dose (pg/mL) | $AUC_{0-t}$/dose (pg × h/mL) |
|---|---|---|---|---|---|---|---|---|
| 1 | 12 | 1127.8 | 8744.8 | 9287.9 | 5.9 | 16.4 | 125.3 | 971.6 |
| 2 | 18 | 484.7 | 9070.4 | 9713.9 | 5.3 | 21.2 | 53.9 | 1007.8 |
| 3 | 16 | 960.4 | 16569.5 | 20388.6 | 10.7 | 24.6 | 106.7 | 1841.1 |
| 4 | 16 | 949.3 | 14563.4 | 18683.2 | 10.9 | 28.1 | 105.5 | 1618.2 |
| 5 | 6 | 1692.8 | 11852.4 | 12202.8 | 3.9 | 13.9 | 188.1 | 1316.9 |
| 6 | 7 | 1472.5 | 8374.0 | 10125.7 | 11.5 | 18.3 | 163.6 | 930.4 |
| 8 | 14 | 1350.7 | 9282.6 | 9857.2 | 5.7 | 16.6 | 150.1 | 1031.4 |
| 9 | 6 | 894.9 | 5957.2 | 6608.2 | 5.0 | 13.5 | 99.4 | 661.9 |
| 10 | 24 | 924.5 | 18026.7 | 30408.7 | 15.7 | 37.5 | 102.7 | 2003.0 |
| 11 | 6 | 4227.2 | 35119.3 | 42027.4 | 11.1 | 22.3 | 469.7 | 3902.2 |
| 12 | 16 | 941.3 | 8946.6 | 9458.5 | 5.9 | 20.2 | 104.6 | 994.1 |
| 107 | 18 | 1159.2 | 16164.1 | 18412.6 | 6.4 | 24.4 | 128.8 | 1796.0 |
| PP population, N = 12 | | | | | | | | |
| MEAN | 13.3 | 1348.8 | 13555.9 | 16431.2 | 8.2 | 21.4 | 149.9 | 1506.2 |
| SD | 5.9 | 958.8 | 7816.9 | 10519.8 | 3.7 | 6.8 | 106.5 | 868.5 |
| CV % | 44.5 | 71.1 | 57.7 | 64.0 | 44.7 | 31.5 | 71.1 | 57.7 |
| MIN | 6 | 484.7 | 5957.2 | 6608.2 | 3.9 | 13.5 | 53.9 | 661.9 |
| MAX | 24 | 4227.2 | 35119.3 | 42027.4 | 15.7 | 37.5 | 469.7 | 3902.2 |
| N | 12 | 12 | 12 | 12 | 12 | 12 | 12 | 12 |
| PP-control population, N = 11* | | | | | | | | |
| MEAN | 12.8 | 1427.3 | 13963.7 | 17041.8 | 8.4 | 21.4 | 158.6 | 1551.5 |
| SD | 6.0 | 964.3 | 8063.4 | 10807.8 | 3.7 | 7.1 | 107.1 | 895.9 |
| CV % | 46.7 | 67.6 | 57.7 | 63.4 | 44.0 | 33.1 | 67.6 | 57.7 |
| MIN | 6 | 894.9 | 5957.2 | 6608.2 | 3.9 | 13.5 | 99.4 | 661.9 |
| MAX | 24 | 4227.2 | 35119.3 | 42027.4 | 15.7 | 37.5 | 469.7 | 3902.2 |
| N | 11 | 11 | 11 | 11 | 11 | 11 | 11 | 11 |

*Subject 02 not included in calculations

TABLE 4

Main Budesonide PK Parameters after Administration of MMX™ 6 mg Extended Release Tablets T2

| Subject | $T_{max}$ (h) | $C_{max}$ (pg/mL) | $AUC_{0-t}$ (pg × h/mL) | $AUC_{0-\infty}$ (pg × h/mL) | $t_{1/2}$ (h) | MRT (h) | $C_{max}$/dose (pg/mL) | $AUC_{0-t}$/dose (pg × h/mL) |
|---|---|---|---|---|---|---|---|---|
| 1 | 14 | 498.1 | 4095.2 | 4617.4 | 6.9 | 19.1 | 83.0 | 682.5 |
| 2 | 16 | 1197.4 | 16173.8 | — | — | — | 199.6 | 2695.6 |
| 3 | 7 | 1146.8 | 11999.5 | 13717.5 | 9.3 | 20.5 | 191.1 | 1999.9 |
| 4 | 10 | 1330.4 | 9354.8 | 10383.5 | 5.9 | 13.7 | 221.7 | 1559.1 |
| 5 | 9 | 1938.4 | 13755.9 | 14299 | 6.4 | 12.5 | 323.1 | 2292.7 |
| 6 | 6 | 1300.4 | 8986.8 | 9398.9 | 3.9 | 11.7 | 216.7 | 1497.8 |
| 8 | 10 | 1781.2 | 14493.0 | 15234.8 | 6.9 | 13.1 | 296.9 | 2415.5 |
| 9 | 7 | 400.8 | 3314.1 | 3643.1 | 3.3 | 12.4 | 66.8 | 552.4 |
| 10 | 14 | 869.6 | 12647.3 | 15596.5 | 11.7 | 25.0 | 144.9 | 2107.9 |
| 11 | 8 | 1948.6 | 16309.7 | 17261.7 | 5.8 | 14.5 | 324.8 | 2718.3 |
| 12 | 12 | 672.6 | 6511.4 | 7292.6 | 4.7 | 15.3 | 112.1 | 1085.2 |
| 107 | 24 | 817.2 | 12178.1 | 15424.7 | 7.9 | 28.9 | 136.2 | 2029.7 |

TABLE 4-continued

Main Budesonide PK Parameters after
Administration of MMX™ 6 mg Extended Release Tablets T2

| Subject | $T_{max}$ (h) | $C_{max}$ (pg/mL) | $AUC_{0-t}$ (pg × h/mL) | $AUC_{0-\infty}$ (pg × h/mL) | $t_{1/2}$ (h) | MRT (h) | $C_{max}$/dose (pg/mL) | $AUC_{0-t}$/dose (pg × h/mL) |
|---|---|---|---|---|---|---|---|---|
| PP population, N = 12 | | | | | | | | |
| MEAN | 11.4 | 1158.5 | 10818.3 | 11533.6 | 6.6 | 17.0 | 193.1 | 1803.0 |
| SD | 5.1 | 532.4 | 4401.6 | 4738.5 | 2.4 | 5.7 | 88.7 | 733.6 |
| CV % | 44.4 | 46.0 | 40.7 | 41.136. | 8 | 33.7 | 46.0 | 40.7 |
| MIN | 6 | 400.8 | 3314.1 | 3643.1 | 3.3 | 11.7 | 66.8 | 552.4 |
| MAX | 24 | 1948.6 | 16309.7 | 17261.7 | 11.7 | 28.9 | 324.8 | 2718.3 |
| N | 12 | 12 | 12 | 11 | 11 | 11 | 12 | 12 |
| PP-control population, N = 11* | | | | | | | | |
| MEAN | 11 | 1154.9 | 10331.4 | 11533.6 | 6.6 | 17.0 | 192.5 | 1721.9 |
| SD | 5.1 | 558.2 | 4264.1 | 4738.5 | 2.4 | 5.7 | 93.0 | 710.7 |
| CV % | 46.4 | 48.3 | 41.3 | 41.1 | 36.8 | 33.7 | 48.3 | 41.3 |
| MIN | 6 | 400.8 | 3314.1 | 3643.1 | 3.3 | 11.7 | 66.8 | 552.4 |
| MAX | 24 | 1948.6 | 16309.7 | 17261.7 | 11.7 | 28.9 | 324.8 | 2718.3 |
| N | 11 | 11 | 11 | 11 | 11 | 11 | 11 | 11 |

*Subject 02 not included in calculations

Pharmacokinetic Results:

After administration under fasting conditions in 3 consecutive study periods of a single dose of Budesonide MMX™ extended release tablets 9 mg (T1), 6 mg (T2) and Entocort® EC 3×3 mg capsules (R) the PK of budesonide was found significantly different. Mean±SD (CV %) of plasma budesonide and urine budesonide-metabolite PK parameters are summarised in the table below for the PP population (N=12).

Results obtained in the present study on the PP population (see table above) were confirmed by the results of the PK analysis on the PP-control population (i.e. after excluding subject randomisation Nr. 02, who showed pre-dose detectable levels) and therefore were regarded as the primary results of the study, as per protocol. Inter-subject variability was higher for the MMX™ tablet formulation than for Entocort® EC, a finding that can be explained by the broader intestinal tract involved in the drug release from the test products (whole colon and sigmoid) as compared to the reference (terminal ileum, ascending colon) and from the absence of dose fractionation in the MMX™ formulations.

Although budesonide elimination is constant and no differences among formulations were found for $t_{1/2}$ values, the different release/absorption behaviour of MMX™ tablets and Entocort® EC capsules was apparent from MRT values which were higher for the MMX™ formulations.

Analysis on T1 and R $C_{max}$. and $T_{max}$, showed a different rate of absorption for MMX™ tablets 9 mg (T1) with respect to Entocort® EC 3×3 mg capsules (R). T1 had a lower budesonide concentration peak than R as confirmed by a PE % of 79% and 90% CI limits of 63%-100%, and a significantly higher $T_{max}$. (13.3 h for T1 vs. 4.8 h for R). Extent of absorption calculated from the $AUC_{0-t}$ of budesonide after administration of T1 and R was also significantly different. T1 bioavailability over the 36 h period was lower than R bioavailability (PE=91%; 90% CI limits: 77%-108%). Therefore, T1 and R were found to be non-bioequivalent.

Analysis on $T_{max}$, and dose-normalized $C_{max}$/dose and $AUC_{0-t}$/dose showed differences in rate and extent of absorption also for T1 vs. T2, As expected, T1 had a higher concentration peak and bioavailability than T2, although a linear relationship with dose was not observed (PE for $C_{max}$/dose=75%; 90% CI limits: 59%-95%, PE for $AUC_{0-t}$/dose=80%; 90% CI limits: 67%-94%). Therefore, T1 and T2 were found non-bioequivalent.

$T_{max}$ differences between T1 and T2 were not statistically significant (p value from t test=0.2244). Analysis on budesonide metabolite urinary excretion ($Xu_{0-36h}$), showed a different excretion among formulations, with a bioequivalence not satisfied for T1 vs. R (PE=66%; 90% CI limits: 54%-81%) and almost achieved for T1 vs. T2 (PE=96%, 90% CI limits: 79%-117%).

Safety Results:

The safety profile of the 3 formulations was similar. Only 3 AEs occurred during the study, 1 with T2 formulation and 2 with R formulation. Of these 3 AEs, only 1 with R formulation (i.e. headache) was judged possibly related to treatment. No meaningful effect of treatment on vital signs, ECGs or laboratory parameters was observed.

Conclusions:

The formulation Budesonide MMX™ extended release tablets 9 mg was found not bioequivalent to the reference Entocort® EC 3×3 mg capsules in terms of rate and extent of bioavailability since the 90% CI for $C_{max}$ and $AUC_{0-t}$ did not fall within the 80%-125% limits required by current guidelines, and $T_{max}$, was statistically different between MMX™ 9 mg and Entocort® EC 3.times.3 mg. This finding is explained by the different release behavior of the test and reference formulations which determines different profiles of budesonide absorption. When MMX™ 9 mg and 6 mg tablet formulations were compared to evaluate dose proportionality, whereas no significant difference was found for $T_{max}$, the analysis of dose normalized $C_{max}$, $AUC_{0-t}$ indicated lack of equivalence since the 90% CI for these parameters did not fall within the 80%-125% limits required by current guidelines. but overlapped them.

The safety profile of the 3 formulations was similar and very good.

Pharmaco-Scintigraphic and Kinetic Study

A single dose, pharmaco-scintigraphic and kinetic study of the gastrointestinal transit and release of a $^{152}$Sm-labelled controlled release formulation of budesonide in 12 fasting male healthy volunteers is carried out.

The objective of the study is to demonstrate and quantify, by pharmaco-scintigraphy and PK analysis, the release and absorption of budesonide in the target region.

Each subject received 1 tablet of budesonide MMX™ 9 mg and an average radioactivity dose of 1.118+0.428 MBq as $^{153}Sm_2O_3$ To define the GI transit behavior of the study formulation, images were recorded at approximately 20 min intervals up to 3 h post-dose and 30 min intervals up to 10 h. Further acquisitions were taken at 12 and 24 h post-dose. The following Regions of Interest (ROIs) were defined: stomach, small intestine, terminal ileum, ileo-caecal junction and caecum, ascending, transverse, descending and sigmoid colon. Quantification of the distribution were achieved by measuring the count rates recorded from the ROIs.

Budesonide plasma levels were detected between the $1^{st}$ and the $12^{th}$ h post-administration. On the average the appearance of drug plasma levels occurred in 6.79±3.24 h ($T_{lag}$). Peak time ($T_{max}$) averaged 14.00±7.73 h, with mean concentration ($C_{max}$) of 1768.7±1499.8 pg/mL. Measured average plasma $AUC_t$ in 24 h was 15607±14549 pg×h/mL. The difference $T_{max}-T_{lag}$ accounted for 7.21±5.49 h, a time period which may be representative of the release time of the active from the tablet.

The following Table 5 summarizes the main kinetic evidence:

TABLE 5

| N = 12 | $C_{max}$ (pg/mL) | $T_{max}$ (h) | $AUC_t$ (pg × h/mL) | $T_{lag}$ (h) | Tmax − $T_{lag}$ (h) |
|---|---|---|---|---|---|
| Mean | 1768.7 | 14.00 | 15607 | 6.79 | 7.21 |
| SD | 1499.8 | 7.734 | 14549 | 3.24 | 5.49 |
| CV | 84.80 | 55.24 | 93.22 | 47.66 | 76.13 |
| Min | 337.3 | 5 | 2465 | 1 | 0 |
| Max | 4756.3 | 24 | 53163 | 12 | 17 |

Combining the scintigraphic with the kinetic evidence, drug absorption during the time interval of the radioactivity location in the target ROI (i.e. the region comprised between the ascending and the descending-sigmoid colon) could be approximately calculated to amount to 95.88%±4.19% of the systemically bioavailable dose.

Results:

The systemic availability of budesonide MMX™ 9 mg is mostly ascribable to the drug absorption throughout the whole colon including the sigmoid, see Table 6 below:

TABLE 6

|  | $AUC_{colon}$ | $AUC_t$ | $AUC_{colon}/AUC_t \times 100$ |
|---|---|---|---|
| Mean | 15113.46 | 15606.52 | 95.88 |
| SD | 14401.79 | 14549.23 | 4.19 |
| Min | 2464.80 | 2464.80 | 84.93 |
| Max | 52376.20 | 53162.50 | 100.00 |

Example 1

2.7 kg of budesonide, 3.0 kg of lecithin (amphiphilic matrix forming material) and 3.0 kg of stearic acid (lipophilic matrix forming material) are mixing after sieving till an homogeneous mixture is obtained; then add 39.0 kg of inert, functional excipients and 9.0 kg of low viscosity hydroxypropylcellulose (binder) and mix for 10 minutes before adding purified water and kneading to a suitable consistence. Then pass the granulate through a rotating granulator equipped with the suitable screen and transfer the granulate to the fluid bed drier to lower the residual moisture content under 3%. After a new sieving on the dry, the granulate is added of 9.0 kg of hydroxypropylcellulose (hydrophilic matrix forming material) and the suitable amount of functional excipients (in particular, microcrystalline cellulose, lactose and silicon dioxide) and, after 15 minutes of mixing, magnesium stearate in a suitable quantity to act as lubricant is added.

After a final blending, tablets of around 300 mg of unitary weight are generated.

The core are then subjected to be coated with a suspension obtained introducing into a stainless steel container 5.8 kg of Eudragit™ (methacrylate copolymers), 0.6 kg of triethylcitrate and 3.0 kg of dyes and talc, using alcohol as solvent.

The mean dissolution percentage (as average of six or more tablets) obtained with this tablet formulation were around 10%-20% at second hour sampling, in the range 25% to 65% at fourth hour and a dissolution greater than 80% was achieved at $8^{th}$ hour sampling.

Example 2

| Component | mg/tablet |
|---|---|
| Tablet | |
| Budesonide | 9.0 |
| Stearic Acid | 10.0 |
| Lecithin | 10.0 |
| Microcrystalline cellulose | 156.0 |
| Hydroxypropylcellulose | 60.0 |
| Lactose monohydrate | 50.0 |
| Silicon dioxide | 2.0 |
| Magnesium stearate | 3.0 |
| Coating materials | |
| Eudragit L100 | 14.0 |
| Eudragit S100 | 12.0 |
| Talc | 7.9 |
| Titanium dioxiede | 4.5 |
| Triethylcitrate | 1.6 |
| Alcohol | q.s. |

The coating of industrial scale tablets of batch MV084 contained 8.0 mg of Eudragit L100 and 8.0 mg of Eudragit S100 (instead of 14.0 mg and 12.0 mg, respectively) with an individual weight of about 330 mg.

According to the present invention, coated tablets individually weighing about 340 mg are obtained.

The above described dissolution test is performed on the tablets of Example 2. The results are the following (indicated as average value):

| after 2 hours at pH 1 | resistant (<5%) |
|---|---|
| after 1 hour at pH 6.4 | resistant (<5%) |
| after 2 hours at pH 7.2 | 15% |
| after 4 hours at pH 7.2 | 37% |
| after 8 hours at pH 7.2 | 91% |

Example 3

Budesonide (3.0 kg) is mixed with soybean Lecithin (5.0 kg) until an homogeneous mixture is obtained. Then carnauba wax (2.0 kg) and stearic acid (2.0 kg) sieved through a fine screen are added. After mixing, the powders are added with other functional excipients and kneaded with a binder solution obtained by dissolving medium viscosity polyvinylpyrrolidone in water. After drying in a fluid bed and milling throughout a suitable screen, hydroxypropylmethyl-cellulose (35.0 kg) and other excipients, including magnesium stearate as lubricant, in a suitable quantity are added and the mixture is blended until an homogeneous powder dispersion is obtained.

The powder mixture is subjected to compression in a rotating tableting machine and the tablets so obtained are coated in a pan coat with a gastroresistant composition containing Eudragit™, plasticizers, dyes and pigments.

According to the present example, coated tablets individually weighing around 105 mg are obtained.

The results of the above described dissolution test are the following (indicated as average value of at least six tablets):

| after 2 hours at pH 1   | resistant (<5%) |
| after 1 hour at pH 6.4  | resistant (<5%) |
| after 2 hours at pH 7.2 | 9%              |
| after 4 hours at pH 7.2 | 28%             |
| after 8 hours at pH 7.2 | 86%             |

Example 4

50 g of diethylene glycol monoethyl ether are homogeneously distributed on 500 g of microcrystalline cellulose; then 100 g of Budesonide are added, mixing to complete homogenization. This mix is further added with 400 g of Budesonide, then dispersed in a blender containing 100 g of carnauba wax and 100 g of stearic acid preheated at a temperature of 60° C. After kneading for 5 minutes, the mixture is cooled to room temperature and extruded in granules of size below 1 mm A suitable mixer is loaded with the matrix granules prepared as above and the following amounts of hydrophilic excipients: 1500 g of hydroxypropyl methylcellulose and 500 g of Policarbophil™ are added. The components are mixed until homogeneous dispersion of the matrices, then added with 2450 g of microcrystalline cellulose, 400 g of lactose, 100 g of colloidal silica and 50 g of magnesium stearate. After further 5 minute mixing, the mix is tableted to unitary weight of 250 mg/tablet.

Tablets are then subjected to coating using a suspension n containing polyacrylate and poly methacrylate copolymers in addition to other dyes, plasticizers and coloring agents in solvent (ethylic alcohol).

The results of the dissolution test performed on these coated tablets are the following (indicated as average value of at least six tablets):

| after 2 hours at pH 1   | resistant (<5%) |
| after 1 hour at pH 6.4  | resistant (<5%) |
| after 2 hours at pH 7.2 | 11%             |
| after 4 hours at pH 7.2 | 32%             |
| after 8 hours at pH 7.2 | 76%             |

Example A 500 g of 5-aminosalicylic-acid and 20 g of octylonium bromide are mixed with 10 g of soy lecithin dissolved in 50 g of a water:ethyl alcohol 1:3 mixture at about 50° C. After homogenization and drying, the granules of the resulting matrix are treated in a kneader with 20 g of carnauba wax and 50 g of stearic acid, heating until homogeneous dispersion, then cold-extruded into small granules. The inert matrix granules are loaded into a mixer in which 30 g of carbopol 971 P and 65 g of hydroxypropyl methylcellulose "are sequentially added." After a first mixing step for homogeneously dispersing the powders, 60 g of microcrystalline cellulose and 5 g of magnesium stearate are added. After mixing, the final mixture is tableted to unitary weight of 760 mg/tablet. The resulting tablets are film-coated with cellulose acetophthalate or polymethacrylates and a plasticizer to provide gastric resistance and prevent the early release of product in the stomach.

The resulting tablets, when subjected to dissolution test in simulated enteric juice, have shown a release of the active principles having the following profile: after 60 minutes no more than 30%, after 180 minutes no more than 60%, after 5 hours no more than 80%.

Example B 50 g of diethylene glycol monoethyl ether are homogeneously distributed on 500 g of microcrystalline cellulose; then 100 g of Budesonide are added, mixing to complete homogenization. This mix is further added with 400 g of Budesonide, then dispersed in a blender containing 100 g of carnauba wax and 100 g of stearic acid preheated at a temperature of 60° C. After kneading for 5 minutes, the mixture is cooled to room temperature and extruded in granules of size below 1 mm.

A suitable mixer is loaded with the matrix granules prepared as above and the following amounts of hydrophilic excipients: 1500 g of hydroxypropyl methylcellulose and 500 g of polycarbophil.

The components are mixed until homogeneous dispersion of the matrices, then added with 2450 g of microcrystalline cellulose, 400 g of lactose, 100 g of colloidal silica and 50 g of magnesium stearate. After further 5 minute mixing, the mix is tableted to unitary weight of 250 mg/tablet.

Example C 850 g of metformin are dispersed in a granulator/kneader with 35 g of diethylene glycol monoethyl ether previously melted with 100 g of stearic acid and 55 g of carnauba wax. The system is heated to carry out the granulation of the active ingredient in the inert matrix. The resulting 1040 g of formulation are added with 110 g of hydroxypropyl methylcellulose and 20 g of magnesium stearate.

The final mixture is tableted to unitary weight of 1170 mg/tablet equivalent to 850 mg of active ingredient.

The resulting tablets, when subjected to dissolution test in simulated enteric juice, have shown a release of the active principles having the following profile: after 60 minutes no more than 35%, after 180 minutes no more than 60%, after 5 hours no more than 80%.

Example D 120 g of octylonium bromide are dispersed in a granulator/kneader with 30 g of stearic acid and 15 g of beeswax in which 10 g of diethylene glycol monoethylene had previously been melted.

The system is heated to carry out the granulation of the active ingredient in the inert matrix. The resulting 10 g of formulation are added with 5 g of hydroxypropyl methylcellulose and 5 g of polycarbophyl, 2 g of magnesium stearate and 3 g of microcrystalline cellulose.

The final mixture is tableted to unitary weight of 200 mg/tablet equivalent to 120 mg of active ingredient.

The resulting tablets, when subjected to dissolution test in simulated enteric juice, have shown a release of the active principles having the following profile: after 60 minutes no more than 25%; after 180 minutes no more than 50%; after 5 hours no more than 70%.

Example E 12 g of diethylene glycol monoethyl ether are loaded on 6 g of microcrystalline cellulose and 6 grams of calcium carbonate, then 100 g of Gabapentin are added and the mixture is homogenized. After that, 800 g of Gabapentin are added which are dispersed in a granulator/kneader with 4.5 g of white wax and 5 g of stearic acid. The system is heated to carry out the granulation of the active ingredient in the inert matrix. The resulting 916.5 g of formulation are added with 39.5 g of hydroxypropyl methylcellulose, 10 g of alginic acid, 11 g of magnesium stearate and 6 g of Syloid. The final mixture is tableted to unitary weight of 1000 mg/tablet equivalent to 900 mg of active ingredient.

Example F 50 g (25 g) of carbidopa and 200 g (100 g) of levodopa are dispersed in a granulator/kneader with 60 g (30 g) of stearic acid and 30 g (15 g) of yellow wax, in which 10 (5) g of diethylene glycol monoethyl ether had previously been melted.

The system is heated to carry out the granulation of the active ingredient in the inert matrix. The resulting 340 g (170 g) of formulation are added with 20 g (10 g) of hydroxypropyl methylcellulose, 10 g (5 g) of xanthan gum, 16 g (8 g) of microcrystalline cellulose, 4 g (2 g) of magnesium stearate.

The final mixture is tableted to unitary weight of 400 (200) mg/tablet equivalent to 50 (25) mg of carbidopa and 200 (100) mg di levodopa.

Example G 4 g of Nimesulide are solubilized in 50 g of diethylene glycol monoethyl ether, then 100 g of microcrystalline cellulose are added to obtain a homogeneous mixture.

The resulting mixture is added in a granulator/kneader with 196 g of Nimesulide, 50 g of stearic acid and 25 g of carnauba wax. The system is heated to carry out the granulation of the active ingredient in the inert and amphiphilic matrix system.

425 g of the resulting granulate are added with 60 g of hydroxypropyl methylcellulose, 5 g of polycarbophil and 10 g of magnesium stearate.

The final mixture is tableted to unitary weight of 500 mg/tablet equivalent to 200 mg of active ingredient.

The resulting tablets, when subjected to dissolution test in simulated enteric juice, have shown a release of the active principles having the following profile: after 1 hour no more than 25%, after 2 hours no more than 40%, after 4 hours no more than 60%, after 8 hours no more than 90%.

Example H 500 g of propionyl carnitine are dispersed in a granulator/kneader with 90 g of stearic acid and 40 g of carnauba wax, in which 20 g of diethylene glycol monoethyl ether had previously been melted. The system is heated to carry out the granulation of the active ingredient in the inert/amphiphilic matrix. The resulting 650 g of formulation are added with 60 g of hydroxypropyl methylcellulose and 10 g of magnesium stearate.

The final mixture is tableted to unitary weight of 720 mg/tablet equivalent to 500 mg of active ingredient.

The resulting tablets, when subjected to dissolution test in simulated enteric juice, have shown a release of the active principles having the following profile: after 60 minutes no more than 40%, after 180 minutes no more than 60%, after 4 hours no more than 80%, after 8 hours no more than 90%.

Example I

One kg of Nimesulide is placed in a high rate granulator, pre-heated to about 70°, together with 200 g of cetyl alcohol and 25 g of glycerol palmitostearate the mixture is kneaded for about 15 minutes and stirred while decreasing temperature to about 30° C. The resulting inert matrix is added, keeping stirring and kneading during cooling, with 50 g of soy lecithin and 50 g of ethylene glycol monoethyl ether. The granulate is extruded through a metallic screen of suitable size and mixed with 50 g of hydroxypropyl methylcellulose, 1320 kg of maltodextrins, 2 kg of lactose-cellulose mixture, 50 g of colloidal silica, 40 g of aspartame, 150 g of citric acid, 75 g of flavor and 65 g of magnesium stearate. The final mixture is tableted to unitary weight of about 500 mg, having hardness suitable for being dissolved in the mouth and a pleasant taste.

Example J

Operating as in the preceding Example, chewable tablets are prepared replacing dextrin with mannitol and the lactose-cellulose mixture with xylitol. The resulting tablets have pleasant taste and give upon chewing a sensation of freshness enhancing the flavor.

Example K

Operating as described in Example I, but with the following components:

| | | |
|---|---|---|
| active ingredient: ibuprofen | mg | 100 |
| lipophilic/inert matrix component: cetyl alcohol | mg | 15 |
| amphiphilic matrix component: soy lecithin | mg | 8 |
| hydrophilic matrix components: mannitol | mg | 167 |
| maltodextrins | mg | 150 |
| methylhydroxypropylcellulose | mg | 30 |
| adjuvants: aspartame | mg | 15 |
| flavour | mg | 5 |
| colloidal silica | mg | 5 |
| magnesium stearate | mg | 5 |

500 mg unitary weight tablets are obtained, which undergo progressive erosion upon buccal administration, and effectively mask the bitter, irritating taste of the active ingredient.

Example L

Operating as described in Example I, but with the following components:

| | | |
|---|---|---|
| active ingredient: diclofenac sodium | mg | 25 |
| lipophilic/inert matrix component: cetyl alcohol | mg | 5 |
| glycerol palmitostearate | mg | 5 |

-continued

| amphiphilic matrix component: soy lecithin | mg | 7 |
| hydrophilic matrix components: xylitol | mg | 168 |
| maltodextrins | mg | 150 |
| hydroxypropylmethylcellulose | mg | 20 |
| adjuvants: aspartame | mg | 5 |
| flavour | mg | 5 |
| colloidal silica | mg | 5 |
| magnesium stearate | mg | 5 |

400 mg unitary weight tablets are obtained, which undergo progressive erosion upon buccal administration, and effectively mask the irritating taste of the active ingredient.

Example M

Operating as described in Example I, but with the following components:

| active ingredient: chlorhexidine | mg | 2.5 |
| lipophilic/inert matrix component: cetyl alcohol | mg | 0.5 |
| glycerol palmitostearate | mg | 0.5 |
| amphiphilic matrix component: diethylene glycol monoethyl ether | mg | 0.3 |
| hydrophilic matrix components: xylitol | mg | 38 |
| maltodextrins | mg | 96 |
| hydroxypropyl methylcellulose | mg | 10 |
| adjuvants: aspartame | mg | 3 |
| flavour | mg | 5 |
| colloidal silica | mg | 2 |
| magnesium stearate | mg | 2 |

150 mg unitary weight tablets are obtained, which undergo progressive erosion upon buccal administration, and effectively mask the irritating taste of the active ingredient.

Example N

One Kg of Nimesulide is placed in a high rate granulator, pre-heated to about 70°, together with g 125 of cetyl alcohol: the mixture is kneaded for about 15 minutes and stirred while decreasing temperature to about 30° C., then added with g 30 of lecithin. The resulting matrix is then extruded through a metallic screen of suitable size and mixed with 2.415 kg of lactose, 1.0 kg of maltodextrins, 50 g of hydroxypropyl methylcellulose, 50 g of colloidal silica, 40 g of aspartame, 150 g of citric acid, 75 g of flavor and 65 g of magnesium stearate. The final mixture is tableted to about 500 mg tablets, having hardness suitable for being dissolved in the mouth and pleasant taste.

What is claimed is:

1. A tablet for the treatment of ulcerative colitis consisting essentially of (1) a tableted core, and (2) a coating on said tableted core, wherein said tableted core consists of a matrix comprising:
   (a) 9 mg of budesonide;
   (b) hydroxypropyl methylcellulose; and
   (c) magnesium stearate;
   wherein said coating on said tableted core comprises methacrylic acid copolymer type A, methacrylic acid copolymer type B, or a mixture of methacrylic acid copolymer type A and methacrylic acid copolymer type B;
   wherein following oral administration of the tablet to a human, the tablet provides an AUC of said budesonide in said human of about 16.43±10.52 (ng)×(h)/mL;
   and wherein said tablet provides extended release of budesonide in the colon of said human effective to treat ulcerative colitis in said human.

2. The tablet of claim 1, wherein said matrix further comprises hydroxypropyl cellulose, silicon dioxide, lactose, microcrystalline cellulose, and lecithin.

3. The tablet of claim 1, wherein said matrix further comprises starch or a starch derivative.

4. The tablet of claim 2, wherein said matrix further comprises starch or a starch derivative.

5. The tablet of claim 1, wherein said matrix does not comprise stearic acid.

6. The tablet of claim 2, wherein said matrix does not comprise stearic acid.

7. The tablet of claim 3, wherein said matrix does not comprise stearic acid.

8. The tablet of claim 4, wherein said matrix does not comprise stearic acid.

9. The tablet of claim 1, wherein said coating on said tableted core comprises a mixture of methacrylic acid copolymer type A and methacrylic acid copolymer type B.

10. The tablet of claim 8, wherein said coating on said tableted core comprises a mixture of methacrylic acid copolymer type A and methacrylic acid copolymer type B.

11. The tablet of claim 9, wherein the weight to weight ratio of said methacrylic acid copolymer type A to said methacrylic acid copolymer type B in said coating on said tableted core is from 1:5 to 5:1.

12. The tablet of claim 11, wherein the weight to weight ratio of said methacrylic acid copolymer type A to said methacrylic acid copolymer type B in said coating on said tableted core is about 1:1.

13. The tablet of claim 10, wherein the weight to weight ratio of said methacrylic acid copolymer type A to said methacrylic acid copolymer type B in said coating on said tableted core is from 1:5 to 5:1.

14. The tablet of claim 13, wherein the weight to weight ratio of said methacrylic acid copolymer type A to said methacrylic acid copolymer type B in said coating on said tableted core is about 1:1.

15. The tablet of claim 1, wherein said coating on said tableted core further comprises triethylcitrate.

16. The tablet of claim 1, wherein following oral administration of the tablet to a human, the tablet provides a $C_{max}$ of said budesonide in said human of about 1.35±0.96 ng/mL.

17. The tablet of claim 7, wherein following oral administration of the tablet to a human, the tablet provides a $C_{max}$ of said budesonide in said human of about 1.35±0.96 ng/mL.

18. The tablet of claim 5, wherein following oral administration of the tablet to a human, the tablet provides a $C_{max}$ of said budesonide in said human of about 1.35±0.96 ng/mL.

19. The tablet of claim 14, wherein following oral administration of the tablet to a human, the tablet provides a $C_{max}$ of said budesonide in said human of about 1.35±0.96 ng/mL.

20. The tablet of claim 1, wherein following oral administration of the tablet to a human, the tablet provides a $T_{max}$ of said budesonide in said human of about 13.3±5.9 hours.

21. The tablet of claim 7, wherein following oral administration of the tablet to a human, the tablet provides a $T_{max}$ of said budesonide in said human of about 13.3±5.9 hours.

22. The tablet of claim 5, wherein following oral administration of the tablet to a human, the tablet provides a $T_{max}$ of said budesonide in said human of about 13.3±5.9 hours.

23. The tablet of claim 8, wherein following oral administration of the tablet to a human, the tablet provides a $T_{max}$ of said budesonide in said human of about 13.3±5.9 hours.

24. The tablet of claim 14, wherein following oral administration of the tablet to a human, the tablet provides a $T_{max}$ of said budesonide in said human of about 13.3±5.9 hours.

25. The tablet of claim 16, wherein following oral administration of the tablet to a human, the tablet provides a $T_{max}$ of said budesonide in said human of about 13.3±5.9 hours.

26. A tablet consisting essentially of (1) a tableted core, and (2) a gastro-resistant coating on said tableted core, wherein said tableted core consists of a matrix comprising:
   (a) 9 mg of budesonide;
   (b) hydroxypropyl methylcellulose;
   (c) magnesium stearate;
   (d) hydroxypropyl cellulose;
   (e) silicon dioxide;
   (f) lactose;
   (g) starch or a starch derivative;
   (h) microcrystalline cellulose; and
   (i) lecithin;
   wherein said gastro-resistant coating comprises methacrylic acid copolymer type A, methacrylic acid copolymer type B and triethylcitrate;
   wherein following oral administration of the tablet to a human, the tablet provides an AUC of said budesonide in said human of about 16.43±10.52 (ng)×(h)/mL;
   and wherein said tablet provides extended release of budesonide in the colon of said human effective to treat ulcerative colitis in said human.

27. The tablet of claim 26, wherein following oral administration of the tablet to a human, the tablet provides a $C_{max}$ of said budesonide in said human of about 1.35±0.96 ng/mL.

28. The tablet of claim 26, wherein following oral administration of the tablet to a human, the tablet provides a $T_{max}$ of said budesonide in said human of about 13.3±5.9 hours.

29. A tablet consisting essentially of (1) a tableted core, and (2) a gastro-resistant coating on said tableted core, wherein said tableted core consists of a matrix comprising:
   (a) 9 mg of budesonide;
   (b) hydroxypropyl cellulose; and
   (c) magnesium stearate;
   wherein said coating on said tableted core comprises methacrylic acid copolymer type A, methacrylic acid copolymer type B, or a mixture of methacrylic acid copolymer type A and methacrylic acid copolymer type B;
   wherein following oral administration of the tablet to a human, the tablet provides an AUC of said budesonide in said human of about 16.43±10.52 (ng)×(h)/mL, a $C_{max}$ of said budesonide in said human of about 1.35±0.96 ng/mL, and a $T_{max}$ of said budesonide in said human of about 13.3±5.9 hour,
   and wherein said tablet provides extended release of budesonide in the colon of said human effective to treat ulcerative colitis in said human.

30. The tablet of claim 29, wherein said matrix further comprises starch or a starch derivative.

* * * * *